United States Patent [19]

Uemura et al.

[11] Patent Number: 5,258,177

[45] Date of Patent: Nov. 2, 1993

[54] IGA PREPARATION AND PROCESS OF MAKING THE SAME

[75] Inventors: Yahiro Uemura, Arcadia; Sunnie Park, Culver City; Raja R. Mamidi, Pomona; Charles M. Heldebrandt, Arcadia, all of Calif.

[73] Assignee: Alpha Therapeutic Corporation, Los Angeles, Calif.

[21] Appl. No.: 804,403

[22] Filed: Dec. 10, 1991

[51] Int. Cl.$^5$ .......................................... A61K 39/395
[52] U.S. Cl. .................. 424/85.8; 530/387.1; 530/388.15; 530/390.1; 530/831; 530/416; 530/419; 530/420; 530/861
[58] Field of Search ............... 530/419, 420, 861, 416, 530/831, 387.1, 388.15, 389.1, 390.1; 424/85.8

[56] References Cited

U.S. PATENT DOCUMENTS

| 4,335,099 | 6/1982 | Funakoshi et al. | 424/85.8 |
|---|---|---|---|
| 4,396,608 | 8/1983 | Tenold | 424/85.8 |
| 4,477,432 | 10/1984 | Hardie | 424/85.8 |
| 4,499,073 | 2/1985 | Tenold | 514/21 |
| 4,820,805 | 4/1989 | Neurath et al. | 530/390.1 |
| 4,876,088 | 10/1989 | Hirao et al. | 424/85.8 |

OTHER PUBLICATIONS

Eibl, et al. *NEJM* 1988, 319:1.
Skvaril, et al. *Coll. Czech. Chem. Comm.*, 1965, 30:2886.
Anderson, et al., *J. Imm.*, 1970, 105:146.
Pejaudier, et al., *Vox. Sang.*, 1972, 23:165.
Kondoh, et al., *Mol. Imm.*, 1987, 24:1219.

*Primary Examiner*—Michael G. Wityshyn
*Assistant Examiner*—C. Sayala
*Attorney, Agent, or Firm*—Sughrue, Mion, Zinn, Macpeak & Seas

[57] ABSTRACT

A method of preparing an IgA rich preparation comprising exposing a plasma fraction to an amino acid, organic salt or inorganic salt with optional chromatographic treatment yielding a product suitable for use in medical conditions treatable with IgA.

16 Claims, 1 Drawing Sheet

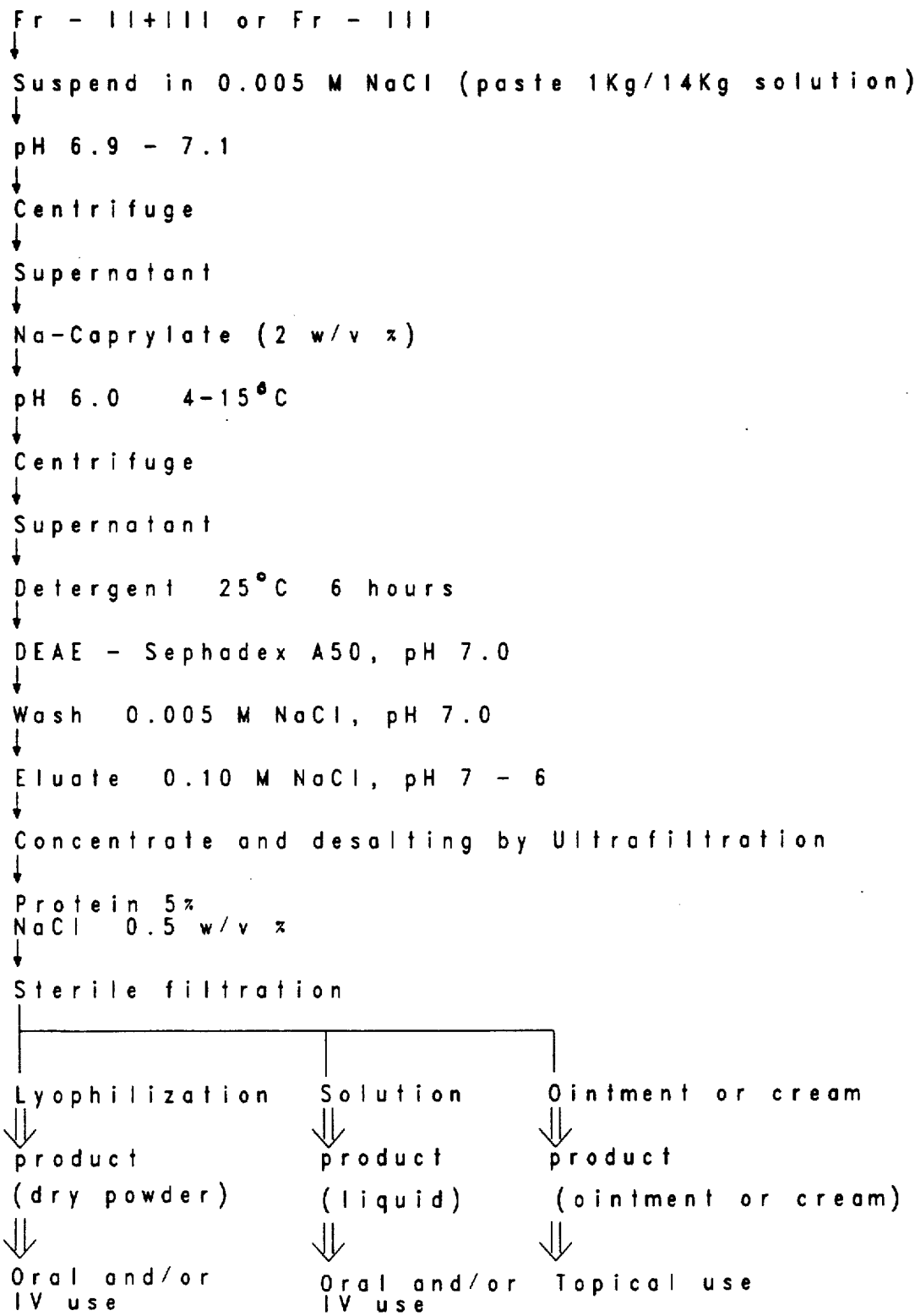

IGA PREPARATION AND PROCESS OF MAKING THE SAME

FIELD OF THE INVENTION

The invention relates to the stable human therapeutic composition for injectable, i.e., intravenous or oral administration, or for topical administration, comprising intact unmodified immunoglobulin A and process of making the same.

BACKGROUND OF THE INVENTION

Of the five major classes of immunoglobulin found in humans, immunoglobulin A (IgA) or secretory immunoglobulin generally is found in serous or mucus fluids Levels of IgA in serum are lower than that of IgG and about twice that of IgM. IgA levels are considerable in the sero-mucous secretion such as saliva, tears, nasal fluids, sweat, colostrum and secretions of the lungs and gastrointestinal tract. It is believed that IgA plays a major role in protecting the exposed epithelium.

It is not uncommon to find IgA in the form of a dimer, joined by a secretory protein which is synthesized by local epithelial cells. Dimers generally comprise antibodies with the same specificity. There are at least two IgA subclasses.

As with the other classes of antibodies, deficiency of IgA can occur transiently, for example in infants when maternal IgA levels wane when breast feeding is discontinued, or permanently, as in the not uncommon occurrence of patients with congenital IgA deficiency. Secretory IgA is known to have a beneficial protective effect on the intestinal mucosa in infants. Stoliar et al., Lancet 1976; i:1258; Williams & Gibbons, Science 1972; 177:697.

Eibl et al. (NEJM 1988; 319:1) found that oral feeding of an IgA-IgG preparation minimized the risk of infants not fed breast milk of contracting necrotizing enterocolitis. The immunoglobulin preparation was made from human serum, Cohn's Fraction II, by ion exchange chromatography. The preparations contained anywhere from 66% to 85% IgA, 15% to 34% IgG and 0.1% to 2% IgM.

Because of the various immunoglobulin deficiencies and the perceived benefits of passively immunizing patients with immunoglobulin deficiency, it is desirable to obtain preparations rich in immunoglobulin, and in particular IgA, for therapeutic uses.

U.S. Pat. No. 4,396,608 teaches a method of preparing an immune serum globulin (IgG) preparation suitable for injection. The method relates generally to preparing IgG rich compositions. A suitable starting material for the process of preparing the IgG rich composition is Cohn's Fraction II or Fraction II plus III. The starting wet paste or powder dissolved in water or physiologic solution is subjected to an acid treatment of about pH 3.5 to 5.0 and thereafter its ionic strength is reduced. All steps are performed at a temperature of 0°-20° C. Protein concentration is adjusted by conventional techniques such as ultrafiltration.

U.S. Pat. No. 4,477,432 relates to an immunoglobulin preparation containing not less than 70% IgG, suitable for oral administration. The immunoglobulin preparation has a pH of about 4-8, is sterile filtered and has a protein concentration of between 5-20%.

U.S. Pat. No. 4,499,073 relates to an immunoglobulin (IgG) preparation prepared by acid treatment wherein the monomer content is greater than about 90%. The starting paste or powder is dissolved in water or physiologic equivalent, the solution is adjusted to a pH of 3.5-5 and the ionic strength is adjusted to a low value.

In view of the apparent advantages of IgA rich preparations for therapeutic purposes it is desirable to have a procedure for obtaining IgA in sufficient quantity, of sufficient purity and suitable for human therapeutic purposes. The above patent references teach methods to obtain immunoglobulin rich preparations in general and those preparations are not necessarily rich in IgA.

Eibl et al., supra, relates to a chromatographic method for preparing an IgA rich preparation.

Skvaril & Brummelova (Coll. Czech. Chem. Comm. 1965; 30:2886) described a method of purifying IgA from the ethanol fraction III of placental serum using zinc salt in combination with ammonium sulphate and gel filtration. Thus, Cohn's Fraction III suspended in cold water was exposed to alumina gel and the eluted protein then was exposed to ammonium sulphate at 40-60% saturation. That cut was removed and dialyzed against water. The remaining proteins were dissolved in acetate buffer. The pass-through from a DEAE-Sephadex separation was obtained and zinc acetate was added to the solution. The precipitate that formed at 4° C. was separated and the supernatant was treated with ammonium sulfate to a concentration of 2.05M. The precipitate was dissolved in water and upon passage through a Sephadex G200 column, fractions containing essentially pure IgA were identified. In vivo studies revealed that the IgA preparations contained trace amounts of IgG but no IgM was noted.

Anderson et al. (J Imm. 1970; 105:146) relates to a one-step isolation of IgA from small volumes of human serum using a bromoacetyl cellulose anti-IgA immunoabsorbent in a batch process. IgA was dissociated from the matrix with acetic acid and then dialyzed against phosphate buffer. The immunoabsorbent, however, is difficult to prepare. The preparations contained from 86% to 98.5% IgA, 0.7% to 11.2% IgG and 0.7% to 5.6% IgM.

Pejaudier et al., (Vox Sang. 1972; 23:165) obtained IgA from Cohn's Fraction III. Several purification schemes were tested. The preferred method comprised extraction of Fraction III with water at pH 5.6, precipitation with caprylic acid in acetate buffer and passage of the supernatant over a DEAE-cellulose matrix with an acetate buffer for elution. The preparations contained trace amounts of IgG and no IgM.

Kondoh et al. (Mol. Imm. 1987; 24:1219) described a procedure for the isolation of human secretory IgA using jacalin lectin. The jacalin was coupled with Sepharose 4B to produce an affinity column. Secreted IgA was obtained from human colostrum. The preparations contained trace amounts of IgM and no IgG.

Thus, it remains desirable to provide a simple procedure for purifying immunoglobulin A in sufficient quantities to produce compositions suitable for therapeutic uses.

SUMMARY OF THE INVENTION

A first object of the invention is to provide a process for producing a human IgA rich preparation.

A second object of the invention is to provide a human IgA rich preparation.

A third object of the invention is to provide a process for producing an IgA rich preparation.

A fourth object of the invention is to provide an IgA rich preparation, preferably at least 50% IgA and of low conductivity.

Those and other objects have been achieved by using an IgA containing composition such as Cohn's Fraction III or Fraction II plus III as a starting material and extracting that starting material with low ionic strength salt solutions such as sodium caprylate or zinc caprylate.

Optionally, the supernatant is passed over an anion exchange matrix, treated to inactivate virus and sterile filtered.

DESCRIPTION OF THE DRAWING

The figure of the Drawing is a flow chart of a preferred embodiment of the present invention.

DETAILED DESCRIPTION OF THE INVENTION

Suitable starting materials are any fluids or fluid concentrates known to contain IgA. A preferred starting material is serum because despite the modest IgA concentration in serum, large quantities of serum can be obtained. The Cohn's Fraction II plus III, and III, pastes of serum are preferred. Preferably, the resultant product of this invention has a plasminogen content testing as less than 0.001 casein unit.

Generally, the Cohn's fractions are obtained as a solid or a paste. The proteins are suspended in a suitable buffer, for example, sodium phosphate ($Na_2HPO_4$) or a sodium chloride solution. A suitable dilution ratio is 1:9 to 1:20 (w/v). The pH is adjusted to about 7.

The suspension can be clarified by low speed centrifugation.

The solution then is extracted with an amino acid, organic salt or inorganic salt at reduced temperature, for example, from about 2° C. to about 20° C., preferably about 2° to 10° C.

Suitable amino acids include phenylalanine, acetyl tryptophan, histidine, glycine, lysine, tryptophan and arginine.

Suitable inorganic salts include NaCl, $KH_2PO_4$, $K_2HPO_6$, $Na_2HPO_4$, $NaH_2PO_4$, $(NH_4)_2SO_4$, $Na_2SO_6$, $ZnSO_6$ and borate.

Suitable organic salts include sodium acetate, sodium citrate, sodium caprylate and zinc caprylate.

The amino acid, organic or inorganic salt is added to a final concentration of about 0.001 to about 0.020M.

The preferred extractant is a caprylate salt, not caprylic acid, such as the aforementioned sodium caprylate and zinc caprylate.

The precipitate formed is separated from the solution, for example by centrifugation or filtration, yielding an IgA rich supernatant. This precipitation step separates unwanted protein including fibrinogen from IgA.

Optionally, the preparation can be treated to inactivate virus, for example, using a solvent or solvent/detergent process. Preferably, the viral inactivation includes contact with a di- or trialkyl phosphate such as tri-n-butyl phosphate (TNBP) with or without a wetting agent such as a non-ionic surfactant. For example, the solution can be treated with about 0.1 to about 0.5% TNBP and about 1 to about 4% TWEEN or about 1 to about 4% TRITON. The solution generally is incubated at about 10°-30° C. for about 1-6 hours at about pH 5-9. See U.S. Pat. No. 4,540,573 and U.S. Pat. No. 4,481,189.

The detergent where needed can be removed by art-recognized procedures such as by ethanol precipitation (using about a 15-30% concentration of ethanol), polyethyleneglycol (at a concentration of about 4% to about 15%) or absorption onto anion exchangers.

Also, optionally, the supernatant can be passed over an anion exchange matrix. Suitable anion exchangers include DEAE and QAE attached to various matrices. For example, DEAE-Cellulose, DEAE-Sephadex (Pharmacia Co.), DEAE-Sepharose (Pharmacia Co.), DEAE-Cellulofine (Chisso Co.), DEAE-Toyopearl (Toyoroshi Co.), QAE-Sephadex (Pharmacia Co.) and QAE-Sepharose (Pharmacia Co.) are preferred.

The absorption onto an anion exchanger is optional and when used, standard chromatography procedures known in the art are practiced. When both the solvent or solvent/detergent process and the anion exchange treatment are employed, it is preferred that the solvent or solvent/detergent process be carried out prior to the anion exchange treatment.

After removing detergent, the resulting solution can be sterilized by filtration and used (with proper dilution as appropriate) as a liquid IgA product for oral and/or IV administration. Where needed, the liquid product can be lyophilized to provide a dry product for later reconstitution.

The product provided herein, in water, has a conductivity of below 100 Mho, preferably below 50 Mho, that is 20 to 40 Mho, and pH of 5.5 to 10.0, preferably 6 to 9. Also, a topical form can be prepared from the solution or lyophilized IgA products as described hereinbelow.

In another embodiment, immunoglobulins can be obtained from a host that is sensitized to a specific pathogen. Thus, the host can be a patient exposed to the pathogen of interest and who exhibits a suitable immunoglobulin response or a non-human animal that is immunized with the pathogen of interest. In the latter case, the artisan can practice a known method for obtaining immunoglobulins from the animal species or suitably modify the claimed method to maximize the recovery of non-human immunoglobulins and suitably modify the non-human immunoglobulins to minimize immunogenicity of the same in the patient, for example remove the $F_c$ portion of the antibodies.

For example, an individual carrying a herpesvirus can serve as a source of herpes-specific IgA. The IgA is purified as described herein and prepared in the form of a topical preparation for direct application to herpes lesions.

The preparation can be suitably diluted with a pharmacologically acceptable diluent to obtain a pharmaceutical composition containing a therapeutically effective amount of IgA that can be administered intravenously, intramuscularly, orally, topically and the like.

The artisan can configure appropriate pharmaceutic compositions containing the IgA rich solution described herein using any of a variety of art-recognized techniques and reagents. For example, to produce a composition suitable for intravenous administration, the IgA rich solution can be mixed with a pharmaceutically acceptable aqueous carrier such as physiologic saline or Ringer's solution. The IgA solution is diluted to a physiologically acceptable level, for example, about a 5% solution.

In another example, the IgA preparation can be administered in a topical form, such as a 1 to 20% IgA (w/w) solution, emulsion, ointment, paste, cream, gel, foam, jelly and the like. Appropriate pharmaceutically acceptable diluents and fillers, binders, lubricants, buffers, preservatives, surfactants, emulsifiers and the like can be incorporated into the final formulation according to art-recognized methods using known materials. Such topical products can be used to treat various infections in humans and other mammals, such as vaginal herpes.

The IgA solution can be made physiologic in pH, approximately 7.2-7.4, and rendered isotonic, approximately 280 milliosmolar immediately prior to use. Pharmaceutically acceptable carriers and excipients can be used in the adjustments and also to provide preservative, handling and other desired features to the solution.

Suitable dosages are derived empirically from, for example, animal studies, clinical trials and other art-recognized foundational experiments. The dosages also will depend on disease severity, patient age, sex and body weight and the like.

Certain aspects of the invention are described in further detail in the following non-limiting examples. Unless noted otherwise, all weight ratios are on a weight-/volume ratio.

Example illustrates a preferred sequence employing in order caprylate salt, solvent/detergent treatment and absorption onto an anion exchanger, without the need for removal of detergent by ethanol precipitation, polyethylene glycol precipitation, etc.

EXAMPLE 1

Cohn's fraction III (Fr. III) paste (100 g) was suspended in a $Na_2HPO_4$ solution (0.002M, 900 ml). The pH was adjusted to 7.2 ±0.1 with normal (1N) HCl or NaOH and the solution was stirred for 2 hrs. at 4° C. The suspension was centrifuged (5000 rpm, 30 min.) to obtain a clear supernatant. The IgA recovery in the supernatant was 95% of the amount of IgA contained in the original Fr. III paste.

Sodium caprylate (20 g) was added to the supernatant and the mixture was stirred for 20 minutes at 4° C. The pH was adjusted to 6.0 ±0.2 by 0.5N HCl and incubated at 4° to 15° C. for 30 to 60 minutes. The precipitate, which appears after pH adjustment, was removed by centrifugation and the supernatant was collected.

The IgA-rich supernatant was concentrated ten times by ultrafiltration. The resulting concentrate was treated with 1% w/v TWEEN-80 and 0.3% w/v TNBP at 25° C. for 6 hrs. to inactivate viruses which might have remained in the source paste. After the viral inactivation, the solution was treated with DEAE-Sepharose to absorb IgA. The DEAE-Sepharose was washed with 0.005M NaCl solution, pH 7.0, before use. The absorption and subsequent washing and elution were performed in a column. The resin was washed with 0.002M NaCl pH 7.0 and the IgA was eluted from the Sepharose using 2% NaCl. For larger scale production, a batch-wise method for absorption, washing and elution would be useful.

The eluted IgA fraction was dialyzed against 0.2% NaCl solution for 20 hours at 4° C. (the NaCl solution was changed three times during dialysis) to adjust salt concentration, pH adjusted to 6 to 8, and lyophilized under sterile conditions. The recovery of IgA was 60% as determined by single radial immunodiffusion method. The percentages of IgA, IgG and other proteins in the final preparation, having a pH of 6 to 8 and low conductivity provided by a 0.2% NaCl content, were 55, 40 and 5%, respectively.

Instead of the dialysis method, salt concentration can be adjusted by employing other conventional techniques such as an ultrafiltration (UF) membrane (available from Amicon, Millipore, etc.)

EXAMPLE 2

Fraction II plus III (Fr. II+III) paste (1 kg) was suspended in a cold (4°-10° C.) NaCl solution (0.001M, 9 l) and stirred to obtain complete dissolution. Sodium caprylate (250 g) was added to the suspension and the pH was adjusted to 6.0 with 1N NaOH or HCl. Following incubation at 10° C., the resulting precipitate was removed by centrifugation (5000 rpm×30 min.).

The IgA recovery of the centrifuged supernatant was 90% of that contained in the original paste.

TWEEN-80 (1%) and TNBP (0.3%) were added to the supernatant. The pH was adjusted to 7.0-8.0 with 1N NaOH or HCL and the solution was incubated at 25° C. for 6 hrs.

After the incubation, polyethylene glycol #4000 (PEG) was added to the solution (final concentration of 6% w/v) and the clear supernatant was collected following centrifugation (5000 rpm×30 min.). PEG was added to the supernatant (final concentration of 15%) and the precipitate (IgA-rich fraction) was collected. The precipitate was washed with the 15% PEG solution several times to assure complete removal of the detergents.

The IgA rich fraction was dissolved in sterile water and lyophilized under sterile conditions.

The final-recovery of IgA was 65%. The percentages of IgA, IgG and other proteins in the final preparation, having a pH of 6 to 7, were 65, 30 and 5%, respectively.

EXAMPLE 3

Fr. II+III paste (1 kg) was suspended in cold NaCl as in Example 2. The pH was adjusted to 7.0-7.2 with N-NaCl or HCl and insoluble particles were removed by filtration using CTX10C filter pad available from KUNO.

Sodium caprylate (150 g) was added to the filtrate, the pH was adjusted to 6.0 with N-HCl and the precipitate was removed by filtration.

The protein concentration was adjusted to 3-5% and then TWEEN-80 (1% w/v) and TNBP (0.3% w/v) were added to the solution. The pH was adjusted to 7.0 with N-NaOH and the solution was incubated at 25° C. for 6 hrs.

DEAE-Sephadex, conditioned with 0.005 mM NaCl, pH 7.0, was added to the solution. More than 80% of IgA was absorbed to the Sephadex resin. The resin was washed several times with 0.005M NaCl buffer to remove TWEEN-80, TNBP and impurity proteins. The IgA was eluted using 100 mM NaCl. The eluate (IgA-rich solution) was concentrated to a 5% solution by UF membrane and the ionic strength also adjusted to lower than 100 mM NaCl.

After sterile filtration and lyophilization, the IgA product, having a pH of about 6.0, was found to be non-pyrogenic in the rabbit (100 mg/Kg rabbit).

The IgA-rich products of the above examples can be used to formulate compositions in aqueous medium containing human IgA 40-90% w/v, human IgG 0-60% w/v and human IgM 0-5% w/v, with conductivity and pH ranges as above disclosed of less than 100 mM, and pH of 5.5 to 10.0.

The Figure of the Drawing depicts a schematic flow chart of a preferred method of the present invention.

The Cohn's Fr. II plus III or Fr. III paste is suspended in 0.005M NaCl at 1 Kg paste per 14 Kg of salt solution. pH is adjusted to 6.9 to 7.1 and the suspension stirred for about 2 hours at 4° C. Then, the suspension is centrifuged to obtain a clean supernatant. Sodium caprylate is added to the supernatant in a concentration of 2% (w/v) with stirring for 1 hour at 10° C. pH is adjusted to 6.0 with HCl, while the solution is held at 4° to 15° C. A precipitate appears which is removed by centrifugation. The supernatant is treated for virus inactivation using a solvent/detergent process at 25° C. for 6 hours. Next, the IgA is absorbed on DEAE-Sephadex A50 previously washed with 0.005M NaCl solution of pH 7.0. The Sephadex is washed with additional 0.005M NaCl solution of pH 7.0. Thereafter, the IgA is eluted by 0.10M NaCl solution of pH 6 to 7, and is concentrated and desalted by ultrafiltration followed by adjustment of protein content to 5% w/v and NaCl content to 0.5% w/v. After sterile filtration, the resultant solution can be used as a liquid product, lyophilized to a dry powder or employed in the preparation of a topical medicament.

EXAMPLE 4

To determine the efficacy of virus inactivation and elimination, the following was conducted. Five viruses were added individually prior to the following noted steps of the IgA purification procedure and virus potency was tested before and after each step.

The five viruses were, Vesicular stomatitis (VSV), chikungunya (CHV), sindbis (SV), Echo and human immunodeficiency-1 (HIV-1). The viruses were added at $10^5$–$10^7$ units prior to the following steps and testing carried out as described in Uemura, et al., Vox Sano 56:155 (1989).

| 1st step: | Fr. II plus III suspension in 0.005M NaCl |
| --- | --- |
| 2nd step: | Extract before caprylate treatment |
| 3rd step: | TWEEN-80 and TNBP treatment |
| 4th step: | PEG 6% fractionation |
| 5th step: | Lyophilization |

Before and after the purification steps, virus potencies (remaining virus antigen or remaining infectious potency) were tested. The inactivation (or elimination) rates were $>10^5$ at each step for each tested virus.

| Virus inactivation and elimination during the purification process. | | | | | |
| --- | --- | --- | --- | --- | --- |
| Purification Step | HIV-1 | VSV | CHV | SV | Echo |
| 1st Fr. II + III extraction | $>10^5$ | $>10^5$ | $>10^5$ | $>10^5$ | $>10^5$ |
| 2nd Caprylate precipitation | $>10^5$ | $>10^5$ | $>10^5$ | $>10^5$ | $>10^5$ |
| 3rd SD treatment | $>10^5$ | $>10^5$ | $>10^5$ | $>10^5$ | NT |
| 4th PEG 6% | $>10^5$ | $>10^5$ | $>10^5$ | $>10^5$ | $>10^5$ |
| 5th Lyphilization | NT | NT | NT | NT | $>10^5$ |
| Accumulated inactivation rate | $>10^{20}$ | $>10^{20}$ | $>10^{20}$ | $>10^{20}$ | $>10^{20}$ |

NT: Not tested.

The artisan will appreciate that the methods and compositions of the instant invention are capable of being incorporated in the form of a variety of embodiments, only a few of which have been illustrated and described herein. The artisan will appreciate that various changes can be made to the invention without departing from the spirit and essential characteristics thereof. The scope of the invention is to be determined by the claims attached hereto.

We claim:

1. A composition comprising an aqueous solution comprising human IgA in an amount of about 40–90% (w/v), human IgG in an amount of about 0 to 60% (w/v) and human IgM in an amount of about 0–5% (w/v), and wherein said solution has a conductivity lower than 50 mM and a pH of between 6–10, wherein said solution comprises plasminogen in an amount less than 0.001 casein unit.

2. The composition of claim 1, wherein the pH is 6 to 9.

3. A method comprising the steps of:
   (a) obtaining a solution comprising IgA having a pH of about 7.0;
   (b) adding to said solution at a temperature of about 2 to 10° C. a caprylate salt to a final concentration of about 0.001 to about 0.020M and then adjusting the pH of the solution to about 6.0;
   (c) incubating the solution of step (b) at said temperature to produce a precipitate and first supernatant; and
   (d) separating said first supernatant from said precipitate to produce an IgA rich solution.

4. The method of claim 3 which further comprises the steps of:
   (e) absorbing said IgA rich solution to an anion exchange resin and washing the resin; and
   (f) separating said anion exchange resin from said IgA rich solution to produce an IgA rich eluate.

5. The method of claim 3 which further comprises the steps of:
   (e) exposing said IgA rich solution to a solution comprising solvent to produce a solvent-containing solution;
   (f) incubating said solvent-containing solution under conditions to inactivate virus therein; and
   (g) removing said solvent from said solvent-containing solution to produce a second supernatant.

6. The method of claim 4, wherein said anion exchange resin comprises DEAE.

7. The method of claim 5, wherein said solvent comprises a di- or tri-alkyl phosphate.

8. The method of claim 3, wherein said solution containing IgA comprises Cohn fraction III or Cohn fraction II plus III.

9. A composition prepared by the method of claim 3.

10. The composition of claim 9 wherein the method further comprises the steps of:
    (e) absorbing said IgA rich solution to an anion exchange resin and washing the resin; and
    (f) separating said anion exchange resin from said IgA rich solution to produce an IgA rich eluate.

11. The composition of claim 9 wherein the method further comprises the steps of:
    (e) exposing said IgA rich solution to a solution comprising solvent to produce a solvent-containing solution;
    (f) incubating said solvent-containing solution under conditions to activate virus therein; and
    (g) removing said solvent from said solvent-containing solution to produce a second supernatant.

12. The composition of claim 10, wherein said anion exchange resin comprises DEAE.

13. The composition of claim 11, wherein said solvent comprises a di- or tri-alkyl phosphate.

14. The composition of claim 9, wherein said solution containing IgA comprises Cohn fraction III or Cohn fraction II plus III.

15. The method of claim 3 wherein said steps (b) and (c) are carried out twice in succession.

16. The method of claim 15 wherein said caprylate salt is sodium caprylate or zinc caprylate.

* * * * *